United States Patent [19]

John

[11] 4,411,273
[45] Oct. 25, 1983

[54] SYSTEM AND METHOD FOR ELECTRODE PAIR DERIVATIONS IN ELECTROENCEPHALOGRAPHY

[76] Inventor: E. Roy John, 930 Greacen La., Mamaroneck, N.Y. 10546

[21] Appl. No.: 873,118

[22] Filed: Jan. 30, 1978

[51] Int. Cl.³ .............................................. A61B 5/04
[52] U.S. Cl. ..................................................... 128/731
[58] Field of Search ..................................... 128/2.1 B

[56] References Cited

U.S. PATENT DOCUMENTS

| | | | |
|---|---|---|---|
| 3,623,477 | 11/1971 | Trent | 128/2.1 B |
| 3,721,230 | 3/1973 | Ziernicki | 128/2.1 B |
| 3,859,988 | 1/1975 | Lencioni, Jr. | 128/2.1 B |
| 4,037,586 | 7/1977 | Grichnik | 128/2.1 B |

Primary Examiner—William E. Kamm
Attorney, Agent, or Firm—Eliot S. Gerber

[57] ABSTRACT

In an electroencephalography system and method, 19 brain wave detection electrodes are removably attached to the scalp of the subject being tested. Using a common reference, such as linked earlobes, each of the electrodes is connected to an amplifier, an analog-to-digital converter and a digital computer, which can be a microprocessor. The digital computer is connected to a magnetic disk or a magnetic tape recorder which records the 19 "monopolar" digitized signals. Subsequently a digital computer will construct any desired electrode derivations, such as derivations from coronal bipolar pairs, sagittal bipolar pairs, or compound electrodes representing a whole hemisphere, by an internal program control. These constructed derivations can be displayed in any desired combination, using a conventional inkwriter or electrostatic matrix printer, or subjected to quantitative analyses. Recording time can be substantially reduced by this method, while comparisons between derivations are facilitated since all data, actual or constructed, were recorded simultaneously.

4 Claims, 2 Drawing Figures

SYSTEM AND METHOD FOR ELECTRODE PAIR DERIVATIONS IN ELECTROENCEPHALOGRAPHY

The Government has rights in this invention pursuant to Grant Number ERP 03494 awarded by the National Science Foundation.

BACKGROUND OF THE INVENTION

The present invention relates to electroencephalography and more particularly to a method and system for comparing the signals from selected pairs of electrodes detecting a subject's brain waves.

It is well known that the brain may produce weak electrical signals both spontaneously and in response to external stimuli. These brain waves may be detected by an electrode contact removably attached to the surface of the head. The electrodes are generally connected by a conductive paste and the system of attaching the electrodes generally follows the International Association 10-20 system which specifies the anatomical points to which the various electrodes should be connected. Those electrical signals generally, at the present time, are amplified and displayed by movements of a pen on a paper in an EEG (electroencephalograph) apparatus. The brain waves (cortical responses) which are present during test periods may be the result of spontaneous brain activity during these periods or may result from external stimuli, i.e., an evoked response, for example, from a flashing light or an audio click.

Neurologists, trained by a long period of study, may monitor the EEG recording and study the paper strip chart and recognize some form of brain injury from those charts. Generally such neurologists operate on a rather subjective or pattern recognition approach and may be able to associate specific wave patterns on the chart with particular types of injury or locations of injury. It has long been recognized that there are not a sufficient number of such skilled neurologists to conduct many of the EEG tests which would be useful in both clinical and screening situations. For example, the EEG analysis is not part of a routine medical examination or even those medical examinations which are used to screen selected personnel.

It has also been suggested that the analysis of the subject's brain waves may be performed by special analog computers, special digital computers or general digital computers which are programmed with a suitable program.

One of the problems that has arisen in the obtaining of brain wave information is that the amount of data which would be useful to be obtained may require an extended testing period. For example, it may be desirable to expose the subject under test to an extensive series of stimuli in order to obtain his responses to the stimuli. Many of the subjects, particularly if they are children or aged, may tire easily, become restless under such extended testing conditions, or change their responses with the familiarization of repetition. Consequently, it is desirable that the test procedures take up as little of the subject's time as possible. In addition, the time of the technician running the test and the time of the test apparatus may both be relatively costly. Consequently, it is again desirable that the test procedure should provide the maximum possible amount of information and at the same time not consume a large amount of the time of the technician or of the testing apparatus.

It has been suggested in the past that, in addition to the brain wave information derived from each individual electrode, valuable information concerning the subject's brain waves may be obtained by comparing the brain waves obtained from one electrode with the brain waves simultaneously obtained from a different electrode.

In the article, "An On-Line Transformation of EEG Scalp Potentials Into Orthogonal Source Derivations," *Electroencephalography and Clinical Neurophysiology*, 1975, it is explained that the scalp may be shown to be made up of 19 concentrated potential fields, each one representing actual currents in the corresponding area of the skull. An electrode will detect the orthogonal activity and the signals may be mapped accordingly. That article is of interest only in showing the use of other than direct measurements.

In the present inventor's prior U.S. Pat. No. 2,696,808 entitled "Method and System for Brain Wave Analysis" there is disclosed a special instrument which considers the two signals from electrodes placed in bilateral symmetric positions on the subject's head. The instrument amplifies the two signals, cross-correlates them, and provides at its output a cross-correlation coefficient of the two signals.

In addition, it has been suggested that a comparison between the signals from two electrodes may be obtained by connecting the electrodes as the inputs to a difference amplifier, as is described in U.S. Pat. No. 4,037,586. A difference amplifier produces at its output a signal representing the difference between the two input signals and consequently the difference amplifier would produce a signal representing the difference in the brain wave signals at the two selected electrodes. A major difficulty with this approach, however, is that it may unduly prolong the testing period. For example, if one wishes to obtain a recording of 19 electrodes recorded monopolarly (one at a time) and, in addition, if one wishes to obtain a recording of the difference signals between any selected 9 pairs (bipolar derivations) of tests, the testing period would be doubled for a specified series. If one then wished to obtain another set of comparisons or difference signals between selected electrodes, one would again be required to repeat the entire series of tests.

FEATURES AND OBJECTIVES OF THE PRESENT INVENTION

It is an objective of the present invention to provide a system and method for the simultaneous comparison of the brain wave signals obtainable from any arbitrarily selected pairs or combinations of removable electrodes attached to the head of the subject under test with a minimum testing period.

It is a further objective of the present invention to provide such a method and system in which the subject under test is exposed to a battery of tests only once, to avoid unnecessary familiarization or fatigue, and the time of the technician performing the tests and the apparatus would be conserved.

It is a further objective of the present invention to provide a complete set, for example, 19 monopolar and 19 sagittal bipolar and 19 coronal bipolar derivations, of brain waves obtained from the subject under test using only a single set of presentations of each test condition.

It is a feature of the present invention to provide a method in electroencephalography for the determination of the differences in electrical output representing brain waves between selected pairs of electrodes. The method comprises first removably securing a plurality of electrodes to the head of said subject. Preferably there are 19 such electrodes to detect brain wave electrical activity plus an indifferent reference and a ground electrode. Then a program of external stimuli, such as light flashes, clicks, etc., are automatically presented to the subject to obtain the subject's evoked responses. The brain wave spontaneous or evoked analog signals are simultaneously amplified, the brain wave signals from each of the electrodes being individually amplified. The amplified signals are then converted into digital form. Then the differences between the simultaneous amplified signals between a plurality of selected pairs of electrodes are computed by automatically subtracting one digitalized signal from one electrode of each of the pairs from the digitalized signal from the other electrode of the same said pair. Analogous compound electrodes can be constructed to reveal similarities, differences or averages between the selected anatomical brain regions.

It is a further feature of the present invention to provide a system in electroencephalography for the determination of the differences in electrical output representing brain waves between selected pairs of electrodes removably secured to the head of the subject under test. The system comprises a plurality of electrodes removably secured to the head of said subject. The system also includes means, such as a magnetic disk, magnetic disk recorder, digital computer and a set of stimuli devices, to present a selected program of external stimuli to the subject to obtain the subject's evoked responses. Means are provided for simultaneously amplifying the brain wave signals from each of the electrodes and there are means for converting the amplified signals into digital form. The system also includes means, such as a programmed digital computer, for computing the differences of the simultaneous amplified signals between a plurality of selected pairs of electrodes, including means for automatically subtracting one digitalized signal from one electrode of each of said pairs from the digitalized signal from the other electrode of the same said pair. Sums can similarly be computed, or any desired combination of operations performed.

BRIEF DESCRIPTION OF THE DRAWINGS

Other objectives and features of the present invention will be apparent from the following detailed description of the invention which is taken in conjunction with the accompanying drawings and which provides the inventor's best mode of practicing the invention.

In the drawings.

DETAILED DESCRIPTION OF THE INVENTION

Figure 1:
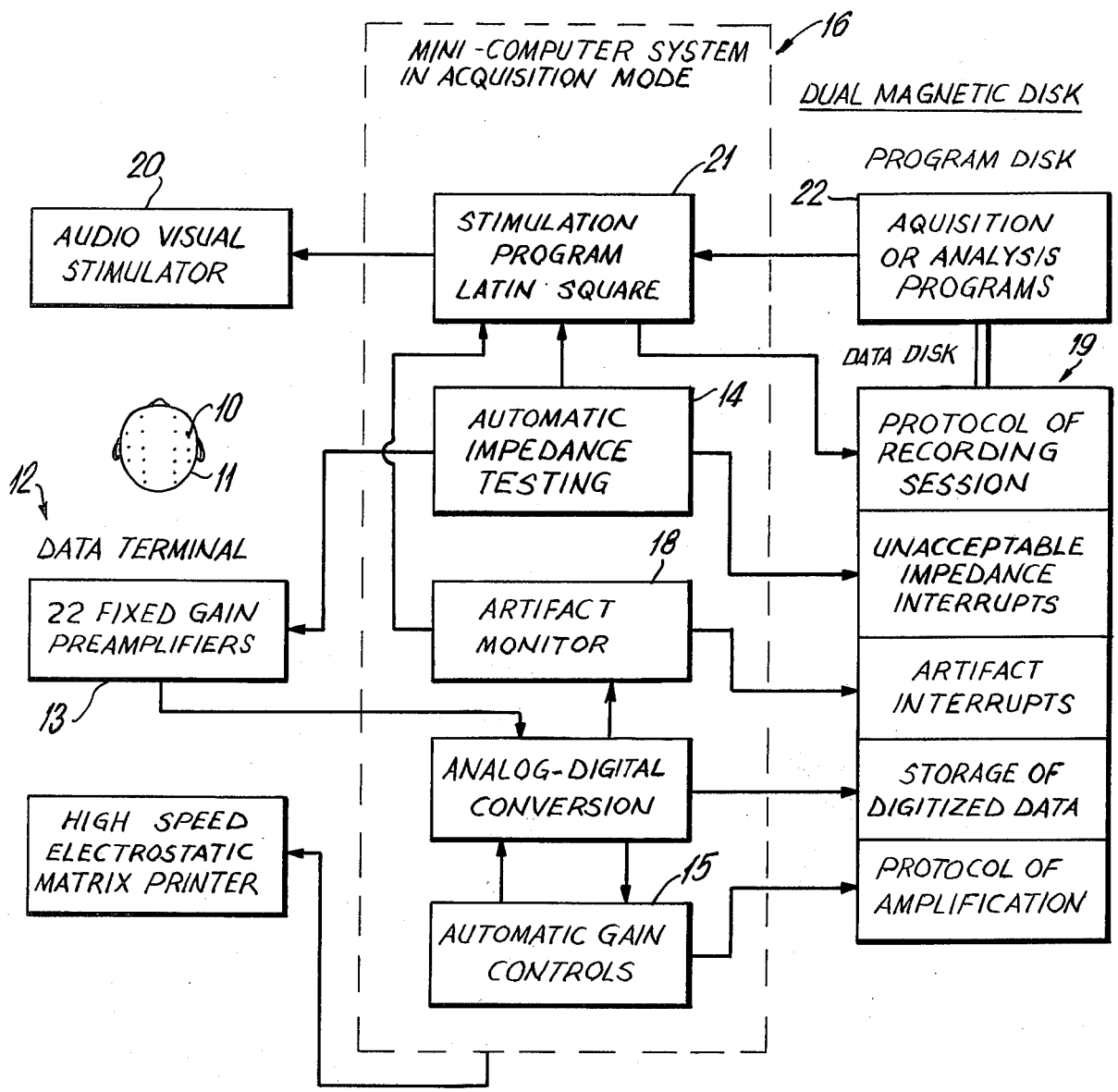
FIG. 1 shows, in block diagram form, the system of the present invention.

As shown in the accompanying FIG. 1, the system of the present invention places a plurality of electrodes 10 on the head 11 of the subject under test. Preferably the electrodes are placed anatomically in accordance with the International Association 10-20 System. That system provides 19 electrodes which are removably attached to the head, preferably by paste, and which provide an indication of the subject's brain waves at the 19 locations on the scalp to which the electrodes are attached.

Each of the electrodes is attached to a data terminal which includes a set of fixed gain preamplifiers 13, with one preamplifier connected to each electrode. There are 19 fixed gain preamplifiers corresponding to the 19 electrodes attached to the head to detect brain waves and three preamplifiers connected to electrodes attached to other portions of the subject to detect muscle artifact, electrocardiogram (EKG) or respiration.

The impedances of the electrodes are automatically tested by automatic impedance testing means 14 to insure that there is a good contact between the scalp of the subject and the electrode. Generally it is preferable that the impedance be below 5000 ohms at each electrode. If the impedance exceeds a predetermined level, for example, 50,000 ohms, the signals from that electrode may be blanked out, i.e., not recorded.

The preamplifiers 13 are connected to the analog-to-digital converter 14. There are a number of commercially available variable gain A-D converters suitable for this purpose. Preferably a single A-D converter is used which, in effect, multiplexes each of the channels and digitizes their output in sequence. The analog digital converter 14 is controlled by an automatic gain control 15 so that each input signal has an individual variable gain up to a factor of 256. The computer system 16 provides a program control gain protocol to set the variable gain for each of the EEG channels. Further details concerning this protocol, as well as other portions of the systems described herein, may be found in the inventor's book, *Functional Neuroscience*, Volume II, "Neurometrics: Clinical Applications of Qualitative Electrophysiology," published 1977 by Lawrence Erlbaum Associates, and particularly its Chapter 4, pages 75 through 85. That volume, and particularly the above-mentioned pages, are incorporated by reference herein.

The computer system 16 may be based on a PDP 11-10 computer or 11-03 microprocessor and includes an artifact monitor 18 which detects and rejects muscle artifact, movements or other amplitude excursions which would tend to distort the brain wave information. The computer system 16 is connected to a multichannel recording media which is preferably a magnetic disk. The disk 19 records, as shown in the figure, the protocol of the recording session, the unacceptable impedance interrupts, the artifact interrupts, the storage of digitized data, and the protocol of the amplification.

The subject under test views an audio-visual stimulator 20. For example, the audio-visual stimulator may be a television screen and, in addition, an audio amplifier and a light flasher. The stimulator 10 provides a programmed set of stimuli to the subject under test, such as a series of grid squares shown on a screen, a series of lights or a series of clicks. The stimulator receives its instructions from the stimulation program 21. Programming of the computer system 16 in its acquisition mode, i.e., when it is acquiring brain wave information from the subject under test, is preferably obtained from a program magnetic disk 22.

In the preferred system and method of the present invention the output from each of the 19 brain wave electrodes is individually recorded, in digital form, in the recording media, i.e., the data disk. That recording is subsequently analyzed in a computer based system. In that analysis the digitized output of each electrode is subtracted from the digitized output of another selected electrode.

Figure 2:
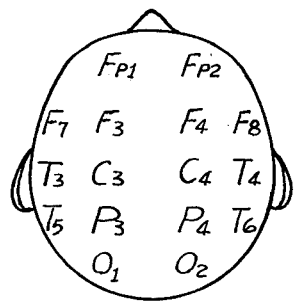
FIG. 2 shows the arrangement of electrodes removably attached to the head of the subject under test.

As shown in FIG. 2, one such subtraction is between left-right adjacent pairs, such as electrodes Fp1, Fp2, giving 19 data pairs (coronal bipolar pairs). A second such subtraction is along anterior-posterior lines, such as electrodes $F_7, T_3$ (sagittal bipolar pairs). These, consequently, will produce a derivation of $2 \times 19$, or 38, data pairs. This provides a total of 57 data computations (19 monopolar, 19 coronal bipolar pairs, 19 sagittal bipolar pairs). These results are obtained under evoked potential (EP) as well as spontaneous fluctuations (EEG).

What is claimed is:

1. A method in electroencephalography for the determination of the differences in electrical output representing brain waves between selected pairs of electrodes, the method comprising:

removably securing a plurality of electrodes to the head of said subject under test;

automatically presenting a selected program of external stimuli to said subject to obtain the subject's evoked responses thereto;

simultaneously amplifying the signals representing brain wave evoked responses from each of said electrodes;

converting the said amplified signals into digital form; and computing the differences of said simultaneous amplified signals between a plurality of selected pairs of electrodes by selecting said pairs so that the same signals from each electrode are used in a plurality of said selected pairs and automatically subtracting one digitized signal from one electrode of each of said pairs from the digitized signal from the other electrode of the same said pair, and displaying the said computed differences.

2. The method of electroencephalography of claim 1 wherein said pairs of electrodes comprises 19 coronal bipolar pairs and 19 sagittal bipolar pairs.

3. A system in electroencephalography for the determination of the differences in electrical output representing brain waves between selected pairs of electrodes removably secured to the head of the subject under test, the system comprising:

a plurality of electrodes removably secured to the head of said subject to detect the brain waves of the subject;

means for presenting a selected program of external stimuli to said subject to obtain the subject's evoked responses thereto;

means for simultaneously amplifying the brain wave signals from each of said electrodes;

means for converting the amplified signals into digital form;

means for computing the differences of said simultaneous amplified signals between a plurality of selected pairs of electrodes, wherein the same signals from each electrode are used in a plurality of said selected pairs, including means for automatically subtracting one digitized signal from one electrode of each of said pairs from the digitized signal from the other electrode of the same said pair; and means for displaying the said computed differences.

4. A system in electroencephalography as in claim 3 wherein said pairs of electrodes comprise 19 coronal bipolar pairs and 19 sagittal bipolar pairs.

* * * * *